United States Patent [19]

Rao

[11] Patent Number: 5,553,625
[45] Date of Patent: Sep. 10, 1996

[54] INTRAVENOUS BLOOD SAMPLING NEEDLE AND INTRAVENOUS THERAPY

[75] Inventor: N. Vasanth Rao, Foster, R.I.

[73] Assignee: Imaging and Display Systems Technology, Inc., Foster, R.I.

[21] Appl. No.: 350,837

[22] Filed: Dec. 7, 1994

[51] Int. Cl.⁶ .................................................. A61B 5/00
[52] U.S. Cl. .......................................... 128/763; 604/52
[58] Field of Search .................... 128/760, 763, 128/765, 770; 604/27, 28, 36, 52, 53, 171, 173, 187, 264, 272

[56] References Cited

U.S. PATENT DOCUMENTS

| | | | |
|---|---|---|---|
| 4,758,225 | 7/1988 | Cox et al. | 604/167 |
| 5,002,066 | 3/1991 | Simpson et al. | 604/52 |
| 5,133,362 | 7/1992 | Moss | 604/264 |
| 5,380,305 | 1/1995 | Ghouri | 604/236 |

*Primary Examiner*—Max Hindenburg
*Attorney, Agent, or Firm*—Christopher S. Schultz

[57] ABSTRACT

A needle for intravenous blood sampling which could be also used for the purpose of intravenous infusion of the patient. Utilizing a unitary structure the needle enables one to perform blood sampling work and intravenous infusion without piercing the patient's skin more than once.

6 Claims, 1 Drawing Sheet

INTRAVENOUS BLOOD SAMPLING NEEDLE AND INTRAVENOUS THERAPY

BACKGROUND OF THE INVENTION

1. Field of the Invention

The invention relates to needles for use in intravenous blood sampling and infusion therapy.

2. Setting of the Invention

In medical care and diagnosis it is very often necessary to take blood samples and introduce intravenous infusion. For, example, if a physician or medical practitioner suspects low blood sugar to be the cause of unconsciousness, or when a patient is in shock and requires blood transfusions, it is almost always the practice to sample the blood before introducing the intravenous infusion. With the equipment available today and the design limitation of this equipment (blood sampling needles and intravenous infusion needles) it is always necessary to puncture the patient's skin twice with the two kinds of needles.

The present invention overcomes the problems of the prior art by providing a single unitary device which performs both blood sampling and intravenous infusion while only piercing the skin once. This accords the patient comfort and the medical carer savings in costs, time and efficiency.

3. Objects of the Invention

Accordingly, it is an object of the present invention to provide a single unitary needle which when used will not subject the patient to the discomfort and pain of two needle punctures when blood sampling and intravenous therapy are called for.

It is another object of the invention to save the medical practitioner time by not requiring two punctures when performing blood sampling and intravenous therapy.

It is another object of the invention to greatly reduce the risk of infection by only requiring a single puncture when performing blood sampling and intravenous therapy.

It is another object of the invention to greatly reduce costs of the hospital since a single needle will perform the task previously carried out by two needles.

It is another object of the invention to reduce the chances of accidental injury and exposure to contagious disease to medical personnel by requiring them to handle a single needle when they previously had to handle two.

These and further objects will become apparent to one having ordinary skill in the art.

SUMMARY OF THE INVENTION

The foregoing objectives are achieved in a needle assembly for sampling blood. The same needle can also be used for intravenous infusion. The needle assembly consists of a sharp hollow needle similar to the one used in conventional blood sampling. The needle is covered with a tubing which is connected to an adapter. This specially designed adapter can be used for the purpose of blood sampling or intravenous infusion.

DETAILED DESCRIPTION OF THE INVENTION

Figure 1:
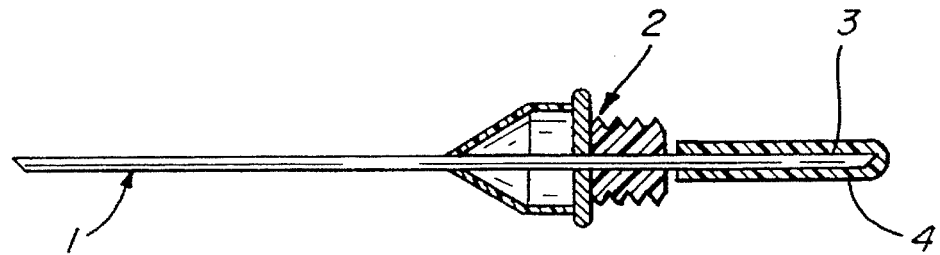
FIG. 1 is a cross section of a blood sampling needle according to the prior art.

Turning now to FIG. 1, a conventional blood sampling needle assembly is shown. The sharp needle 1 which pierces the skin and blood vessel is connected to a subassembly 2 with a threaded crew. The opposite end 3 is covered with a transparent or semi-transparent sheath 4. When the test tube for collecting the blood sample is screwed onto the subassembly 2, the needle point pierces the sheath 4 and drum head of the test tube. The blood is sucked into the test tube and the blood sample is collected.

Figure 2:
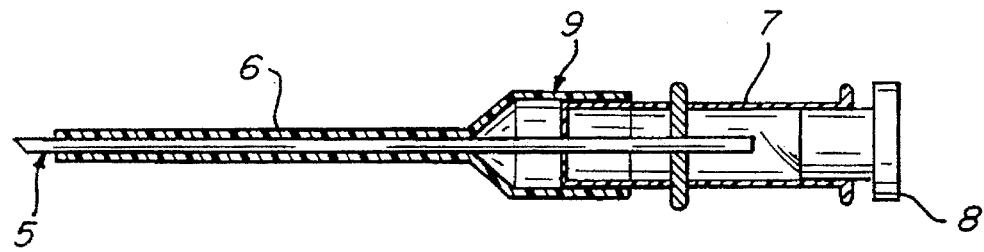
FIG. 2 is cross section of an intravenous infusion needle assembly according to the prior art.

If it is subsequently desired that intravenous transfusion be performed, the prior art utilizes a second needle, different from the first kind, as shown in FIG. 2. In this intravenous infusion needle assembly, the needle 5 pierces the patients skin and blood vessel. This needle is covered with Teflon or other material tubing 6. The other end of the needle is enclosed in a transparent container 7 which enables the blood flow to be seen when the blood vessel is pierced. This container has a cap or cover 8. The subassembly 7 with the needle 5 is pulled out of the patient after the blood vessel is pierced, leaving the Teflon tubing 6, or tubing of another material in the patient's body. Through this tubing the transfusion is performed by attaching transfusion tubing at the assembly 9.

Figure 3:
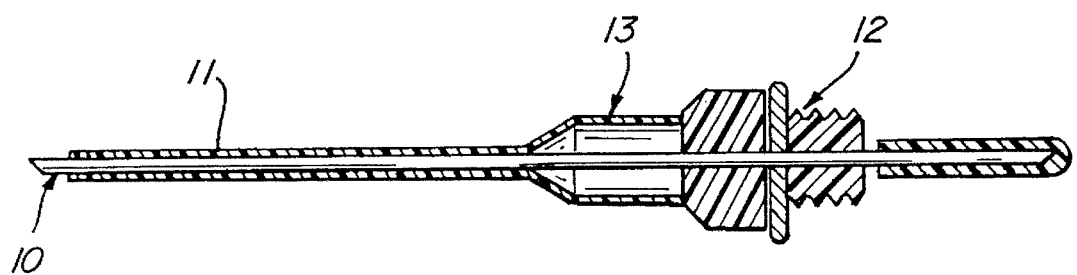
FIG. 3 is a cross section of the dual blood sampling needle and intravenous infusion needle according to the present invention.

In the present invention, as shown in FIG. 3, the two prior art needles and associated procedures are carried out by a single needle assembly. The needle 10 in FIG. 3 for piercing the skin and blood vessel is similar to the needle 1 in FIG. 1. However, this needle is covered with a Teflon tubing 11 or tubing of another suitable material. This outer tubing performs the same function as tubing 6 in FIG. 2. The other end of the needle is connected to the subassembly 12 with the threaded support or other appropriate attachment means to which the blood sampling test tube can be screwed. In this respect, the assembly operates in a fashion similar to the blood sampling procedure using the needle assembly shown in FIG. 1. After the blood sampling procedure is completed by drawing the blood into the container, the container is unscrewed from the needle assembly 12. At this time, if it is required to carry out intravenous infusion procedure, the needle assembly 12 is pulled out of the adapter assembly 13, leaving the tubing 11 in the patient's skin, and the intravenous tubing is inserted into the assembly as is done in the conventional procedure. This invention as described will eliminate the procedure of piercing the skin and blood vessel of the patient twice.

The present invention is to be limited only in accordance with the scope of the appended claims, since those skilled in the art may devise other embodiments within the limits of the claims.

What is claimed is:

1. A needle assembly for use in blood sampling and intravenous infusion comprising:

a blood sampling assembly comprising a needle and a subassembly, said needle being connected to said subassembly, wherein said subassembly comprises attachment means to which a blood sampling test tube can be attached and detached, and an adapter assembly for intravenous infusion comprising a tubing at one end which substantially surrounds said needle, and a transparent container at an opposite end which contacts said subassembly, said container being for revealing blood flow and for connection to infusion tubing, wherein after blood sampling is performed said blood sampling assembly is pulled out of said adapter assembly leaving said tubing in the patient.

2. A needle assembly comprising:

a blood sampling assembly comprising a needle and a subassembly, said needle being connected to said subassembly, wherein said subassembly comprises attachment means to which a blood sampling container can be attached and detached, and an adapter assembly for intravenous infusion comprising a tubing at one end which substantially surrounds said needle, and a container at an opposite end which contacts said subassembly.

3. A method of blood sampling and intravenous infusion comprising the steps of:

inserting a portion of a blood sampling means and a portion of an intravenous infusion means into a subject, wherein said blood sampling means comprises a puncture means, a portion of which is inserted into said subject, and said intravenous infusion means includes a tubing which substantially surrounds said puncture means, such that a portion of said tubing is inserted into the subject along with said puncture means;

drawing a blood sample from said subject using said blood sampling means; and withdrawing said blood sampling means from said subject while leaving said intravenous infusion means in said subject.

4. A method according to claim 3, further comprising attaching said intravenous infusion means to a source of intravenous infusion.

5. The method according to claim 3, said drawing step comprising detaching a container containing said blood sample, from said blood sampling means.

6. A method according to claim 5, further comprising attaching said intravenous infusion means to a source of intravenous infusion.

* * * * *